US00PP21163P2

(12) United States Plant Patent
Blom

(10) Patent No.: US PP21,163 P2
(45) Date of Patent: Jul. 13, 2010

(54) ***CHRYSANTHEMUM* PLANT NAMED 'ZANMUSUNDANCE'**

(50) Latin Name: ***Chrysanthemum×morifolium* Ramat.**
Varietal Denomination: Zanmusundannce

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/314,958

(22) Filed: Dec. 19, 2008

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent L Bell
(74) *Attorney, Agent, or Firm*—Steptoe & Johnson LLP

(57) ABSTRACT

A *chrysanthemum* plant named 'Zanmusundance' characterized by its medium sized blooms with yellow ray florets and prolific branching; natural season flower date October 6–10; blooming for a period of 5 weeks.

3 Drawing Sheets

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmusundance'. 'Zanmusundance' is a product of a breeding and selection program for outdoor pot mums (garden mums) which had the objective of creating new *chrysanthemum* cultivars with a double type inflorescence, a natural season flower date October 6–10; blooming for a period of 5 weeks. 'Zanmusundance' is a seedling resulting from the crossing of female parent id 15069 and male parent id 4917. Plants of 'Zanmusundance' differ from plants of the female parent in growth rate; those of the seedling show a higher rate. Plants of 'Zanmusundance' differ from plants of the male parent in the color of the ray-florets; that of the male parent is white, while that of the seedling is yellow.

The new and distinct cultivar was discovered and selected as a flowering plant by Wilhelmus Bemardus Blom on a cultivated field in Rijsenhout, The Netherlands in 2005. The first act of asexual production of 'Zanmusundance' was accomplished when vegetative cuttings were used from the initial selection in 2005 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
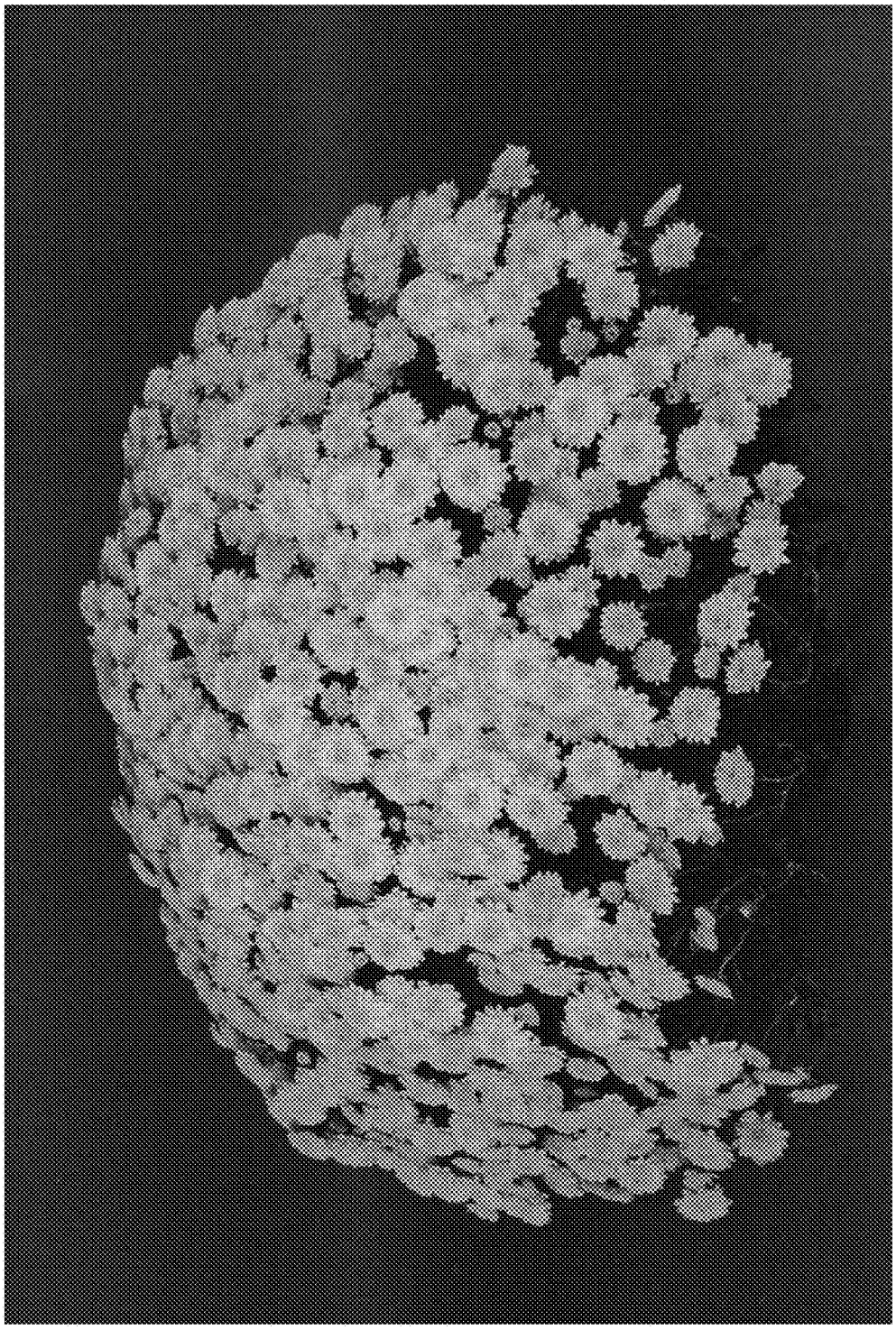
FIG. 1 shows a plant of the cultivar in full bloom.
Figure 2:
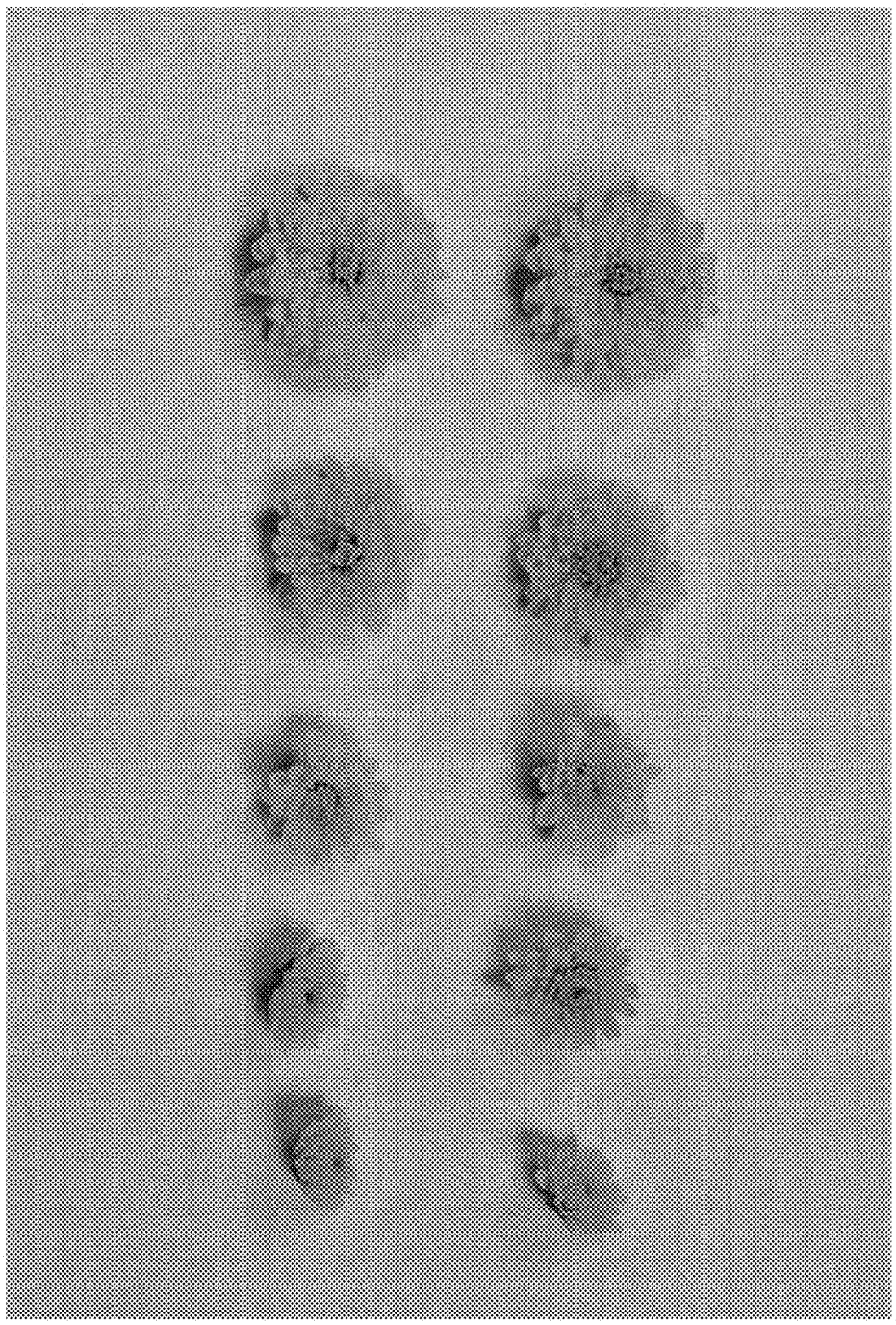
FIG. 2 shows the various stages of bloom of the new cultivar.
Figure 3:
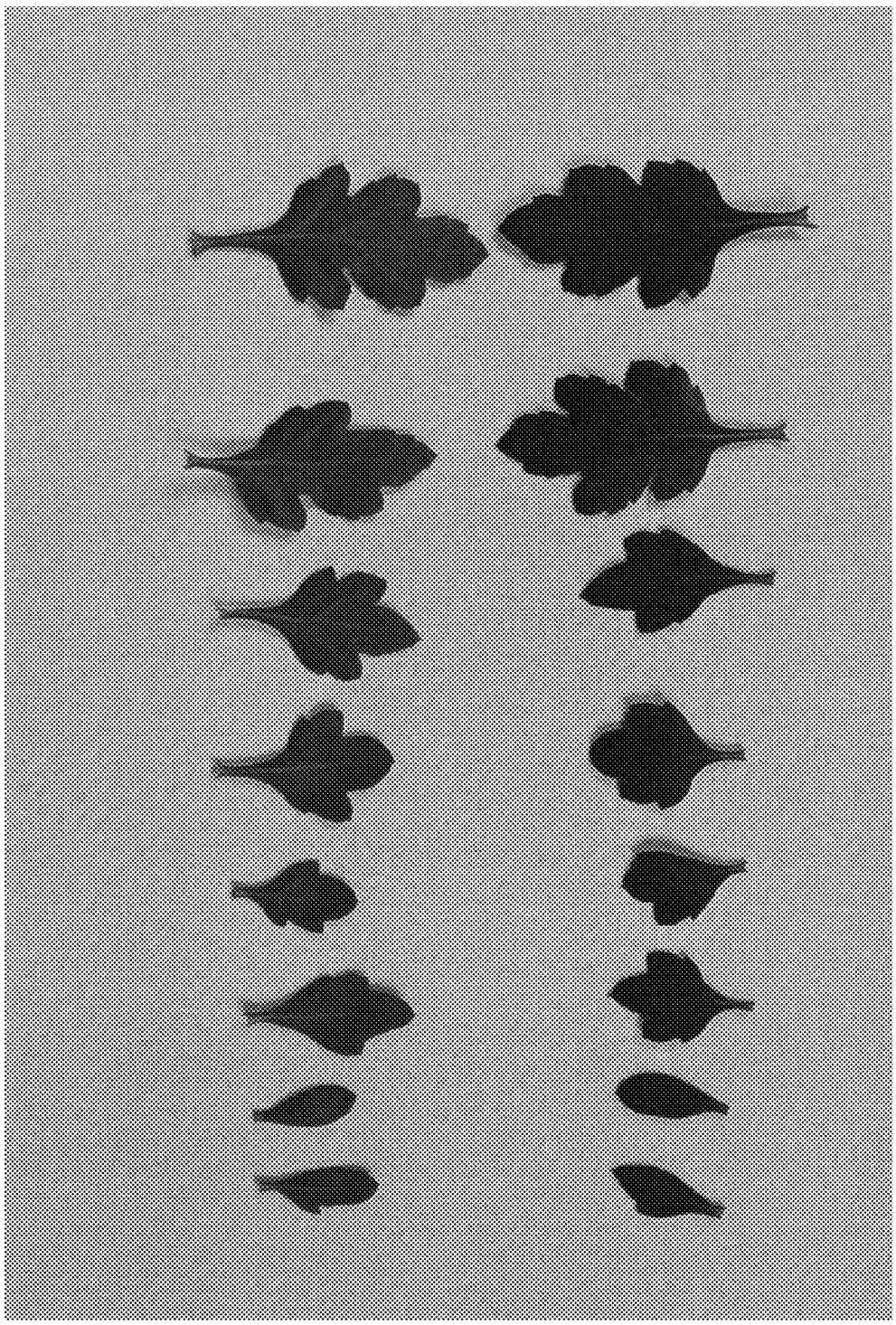
FIG. 3 shows the various stages of foliage of the new cultivar.

The observations and measurements were gathered from plants grown out door in Rijsenhout, The Netherlands under natural day length and temperature and planted in week 22 in 2008. The natural blooming date of this crop was October 6–10. The average height of the plants was 30 cm. No growth retardants were used. No tests were done on disease or insect resistance or susceptibility. No tests were done on cold or drought tolerance. This new variety produces medium sized blooms with yellow ray florets blooming for a period of 5 weeks.

From the cultivars known to inventor the most similar existing cultivar in comparison to 'Zanmusundance' is 'Zanmusundown' (U.S. Plant patent application Ser. No. 12/314,959). When 'Zanmusundown' and 'Zanmusundance' are being compared the following difference is noticed: The difference of 'Zanmusundown' and 'Zanmusundance' are (1) Plant size. And (2) Flower color. (1) The plants of 'Zanmusundown' are smaller than those of 'Zanmusundance' (2) The flower of' Zanmusundown are more deeply yellow colored than those of 'Zanmusundance'.

The following is a description of the plant and characteristics that distinguish 'Zanmusundance' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum* x*morifolium* Ramat. 'Zanmusundance'

| | |
|---|---|
| Bud | |
| Size | Small; cross-section 0.6 cm, height 0.5 cm |
| Shape | Oblate |
| Texture | Pubescent |
| Outside Color | Greyed-green 191A |

TABLE 1-continued

| Botanical Description of *Chrysanthemum* x*morifolium* Ramat. 'Zanmusundance' | |
|---|---|
| Phyllaries | |
| Number | 25-28, arranged in 3 rows |
| Shape | Elliptic |
| Apex | Acute |
| Base | Truncate |
| Margin | Entire |
| Color | Upper side Greyed-green 191A<br>Lower side Greyed-green 191C |
| Length and width | 3 mm; 2 mm |
| Texture | Pubescent |
| Inflorescence | |
| Type | Double |
| Height | 0.5 cm |
| Diameter | 4 cm |
| Peduncle length | 4-6 cm |
| Peduncle color | Green 138B |
| Peduncle diameter | 1 mm |
| Peduncle surface | Pubescent |
| Number per branch | Approx. 7 inflorescences |
| Flowering period individual inflorescence | Ca. 4 weeks |
| Seeds | Produced in small quantities, ovate, Greyed-brown 199A, length 1.5 mm, diameter 0.8 mm |
| Fragrance | Faint *chrysanthemum* odor |
| Color | |
| Center of inflorescence (ray-florets) | Immature stage: Yellow 13A<br>Mature stage: Yellow 13A |
| Color of upper surface of the ray-florets | Yellow 9A |
| Color of the lower surface of the ray-florets | Yellow 8A |
| Tonality from Distance | A garden mum with yellow inflorescences |
| Color of the ray-florets after aging of the plant | Yellow 9D |
| Ray florets | |
| Texture | Upper and lower side smooth |
| Number | 140 |
| Shape | Elliptic |
| Apex | Pointed |
| Base | Obtuse |
| Cross-section | Flat |
| Longitudinal axis of majority | Straight |
| Length of corolla tube | 3 mm |
| Ray-floret margin | Entire |
| Ray-floret length | 1.3-1.5 cm |
| Ray-floret width | 5 mm |
| Ratio length/width | Medium |
| Disc florets | |
| Disc diameter | 1 mm |
| Distribution of disc florets | Scarce, only visible in mature inflorescence |
| Shape | Tubular |
| Color | Yellow 11D at apex, Yellow-green at 150D at base |
| Number | 3-4 |
| Length | 0.5 mm |
| Diameter | 0.3 mm |
| Receptacle | |
| Shape | Conical raised |
| Height | 5 mm |
| Color | Green 138C |
| Diameter | 4 mm |

TABLE 1-continued

| Botanical Description of *Chrysanthemum* x*morifolium* Ramat. 'Zanmusundance' | |
|---|---|
| Reproductive Organs | |
| Androecium | Present on disc florets only |
| Stamen length | 3 mm |
| Stamen color | Yellow-green 144A |
| Anther color | Yellow 3A |
| Pollen | Not observed |
| Gynoecium | Present in both ray and disc florets |
| Style colour | Yellow-green 154C |
| Style Length | 3 mm |
| Stigma colour | Yellow 7A |
| Stigma Width | 1 mm |
| Ovary | Enclosed in calyx |
| Plant | |
| Form | Grown as potmum, outdoor raised and mounded |
| Growth habit | Spherical shape |
| Growth rate | Medium |
| Height | 30 cm |
| Width | 45 cm |
| Stem Color | Greyed-brown 199A |
| Stem Strength | Weak |
| Stem Brittleness | Brittle |
| Stem Anthocyanin Coloration | Not observed |
| Internode length | 1-2 cm |
| Length of lateral branch | From top to bottom 15-17 cm |
| Lateral branch color | Green 137C |
| Lateral branch diameter | 2 mm |
| Lateral branch brittleness | Brittle |
| Branching (average number of lateral branches) | Prolific with 9 breaks after pinching |
| Natural season blooming date | October 6-10 to November 10-14 |
| Foliage | |
| Leaf color | Upper side: Green 139A to Green 139B<br>Lower side: Greyed-green 191B |
| Color midvein | Upper side: Yellow-green 147D<br>Lower side: Yellow-green 148D |
| Size | Small.; length 1.5-4 cm, width 1-2.5 cm |
| Quantity (number per lateral branch) | 15-17 |
| Shape | Elliptic |
| Texture upper side | Sparsely pubescent |
| Texture under side | Pubescent |
| Venation arrangement | Palmate |
| Shape of the margin | Entire to serrated |
| Shape of Base of Sinus Between Lateral Lobes | Acute |
| Margin of Sinus Between Lateral Lobes | Diverging |
| Shape of Base | Acute to truncate |
| Apex | Mucronulate |
| Petiole length | 2-5 mm |
| Petiole diameter | 2 mm |
| Petiole color | Yellow-green 147D |

TABLE 2

| Differences with the comparison variety | | |
|---|---|---|
| | 'Zanmusundance' | 'Zanmusundown' |
| Plant height | 30 cm | 25 cm |
| Plant width | 45 cm | 40 cm |
| Color inflorescence disc | Yellow 13A | Yellow-orange 15A |
| Color upperside ray-florets | Yellow 9A | Yellow 12A |

I claim:

1. A new and distinct variety of *chrysanthemum* plant as described and illustrated.

* * * * *